United States Patent [19]

Green et al.

[11] Patent Number: 5,439,439
[45] Date of Patent: Aug. 8, 1995

[54] METHOD FOR APPLYING ORTHOPAEDIC BANDAGES

[75] Inventors: Richard Green, Livingston; Zale Oser, Bound Brook, both of N.J.

[73] Assignee: Johnson & Johnson Orthopaedics, Inc., Raynham, Mass.

[21] Appl. No.: 726,449

[22] Filed: Jul. 8, 1991

[51] Int. Cl.⁶ ................................. A61F 5/04
[52] U.S. Cl. ............................ 602/6; 602/8; 602/900
[58] Field of Search .................... 128/877, 878, 83, 85, 128/77, 87 R, 156; 604/368, 369, 378, 265; 602/3-8, 41, 44-47, 60, 61, 900, 89 R-91 R

[56] References Cited

U.S. PATENT DOCUMENTS

| | | | |
|---|---|---|---|
| 4,442,833 | 4/1984 | Dahlen | 128/90 |
| 4,589,873 | 5/1986 | Schwarz | 604/265 |
| 4,628,917 | 12/1986 | Campagna | 128/90 |
| 4,793,330 | 12/1988 | Honeycutt | 128/90 |
| 4,856,502 | 8/1989 | Ersfeld | 128/90 |

Primary Examiner—Robert A. Hafer
Assistant Examiner—David J. Kenealy
Attorney, Agent, or Firm—Joseph F. Shirtz

[57] ABSTRACT

The invention is a method of applying a material usable as an orthopaedic bandage which material is an open weave substrate having thereon a curable resin. The resin is curable, for example, by polymerization which polymerization is initiated by immersion of the resin coated substrate in a bath. Gloves are worn during the performance of the method which gloves are provided with a coating which in use is lubricous relative to the resin coated substrate. Thus the interference in application of the substrate due to the substrate sticking to the gloves is substantially reduced or eliminated by the lubricousness of the gloves.

10 Claims, 4 Drawing Sheets

METHOD FOR APPLYING ORTHOPAEDIC BANDAGES

FIELD OF THE INVENTION

The present invention relates to an improved method for applying orthopaedic casting bandages of the type used to form orthopaedic casts. In particular the invention relates to a method for applying orthopaedic bandages of the type having an uncured resin coating thereon.

BACKGROUND OF THE INVENTION

Plaster of paris casts have been used to immobilize body members for some time. These bandages are made by depositing plaster of paris on a reinforcing scrim material such as gauze. When the plaster of paris is dipped in water, reactions take place which result in the hardening of the cast material. Plaster of paris casts, however, suffer from a number of disadvantages. X-ray transmission through the cast to determine whether a fracture has properly set is extremely difficult. In addition, the cast is quite heavy and restricts the mobility of patients wearing the east.

In order to overcome the disadvantages of plaster of paris casts, numerous attempts have been made to develop plastic or plastic reinforced materials as replacements for plaster of paris. U.S. Pat. Nos. 3,241,501 and 3,881,473 disclose casts which are made with a flexible fabric impregnated with a polymer which is capable of being cured by ultraviolet light.

Other attempts to replace plaster of paris casts are disclosed in German Offenlegenschrift numbers 2353212 and 2357931, U.K. Patent #1,578,895, and PCT Application #WO 81/00671. These bandages are open weave fabrics coated with polyurethane prepolymers, that is, reaction products of isocyanates and polyols. The bandages are dipped into water in the same manner as the plaster of paris and then applied to the limb of the patient. The water causes the prepolymer to polymerize and form a rigid polymer structure.

More recently it has been found that in working with such materials having a prepolymer resin coating that the tackiness of the resin of the bandage can make working with the bandages difficult and cumbersome for the doctor. In an attempt to address this issue a glove lubricant comprised of water, sorbitol, mineral oil and silicon fluid has been sold by 3M Company, St. Paul, Minn., under the trade name CastCreme with instructions to apply the lubricant to the gloves of one applying an isocyanate-functional prepolymer coated cast after wrapping of the cast but before molding of the cast to avoid having the exposed casting material adhere to the gloves of the one applying the cast. This is disclosed in the background of U.S. Pat. Nos. 4,667,661 and 4,774,937.

The '661 and '937 patents are directed to addressing the adherence issue by providing the resin itself with a lubricant. The curable resin coated sheet is prelubricated with a lubricant which is either a) bonded to the resin, b) added to the resin or applied to the surface of the coated sheet or c) provided in a combination of the bonding and surface application described. In many instances however, the tacky feature of the orthopaedic bandage is desirable. As by way of example when the applier is attempting to get the end of the bandage to stick to the surface of the bandage wrap in order to terminate the application of the bandage. The addition of lubricant in the resin permits relative slipping of the resin coated sheet and requires molding the cast in position and holding it in position to prevent slippage.

Coatings for substrates having a low coefficient of friction have been shown in U.S. Pat. No. 4,100,309 entitled "Coated Substrate Having a Low Coefficient of Friction Hydrophilic Coating and a Method of Making the Same". That reference describes a substrate which is coated with a polyvinyl pyrollidone-polyurethane inter polymer. In the method, a poly-isocyanate and a polyurethane in a solvent such as methyl ethyl ketone are applied to a substrate and the solvent evaporated. If the substrate is a polyurethane, only the polyisocyanate need be employed. Polyvinyl pyrollidone in a solvent is then applied to the treated substrate and the solvent evaporated. The substance and coated objects described in this reference are used in blood and body contacting environments. In order to lubricate the introduction of devices into openings in the body.

SUMMARY OF THE INVENTION

The present invention provides a method of immobilizing a patient's limb using an orthopaedic bandage material comprising the steps of providing a substrate having a water activatable setting and adhering substance impregnated thereon and immersing such impregnated substrate in a bath of activating solution such as water. The activated substrate is applied to the limb using gloves having a coating thereon which is lubricous in use. That is the gloves are slippery relative to the resin of the impregnated substrate and therefore provide ease of application and conformance of the substrate. The impregnated substrate is then permitted to set in order to adhere and cure.

In a preferred embodiment the substrate is an open weave fibrous structure and the setting and adhering substance impregnated on the substrate is a polyurethane prepolymer. Further the gloves provided for in the method of the invention are donned prior to removing the substrate from the bath. The coating on the gloves may be provided to be dry when supplied but become lubricous when wetted with water and thus immersing the gloves in the bath wets the coating in order to provide the lubricous surface.

A further portion of the invention provides for opening the package after wetting the coating of the gloves thus providing for the gloves to be lubricous prior to at least one application of a bandage.

Furthermore, the gloves may be donned prior to immersing the substrate and the substrate may be immersed in the bath by being held by a hand covered with the gloves thus activating the prepolymer on the substrate and the coating on the gloves at the same time.

In a further form of the invention the method calls for providing an activatable substrate impregnated with a polymerizable material which makes the substrate self-adhering. The polymerizable material is activated by immersion in a bath. That is the polymerization of the polymerizable material is activated by immersion in the bath. Gloves having an outer coating are donned which coating is activated or preferably made more lubricous than in its dry state by the bath in which the substrate is immersed. Thus immersed the gloves are provided with a lubricous surface. Using the gloves, the activated substrate is wrapped about the patient's limb such that the application is assisted by the reduction in tackiness of the substrate relative to the gloves without reducing significantly the tackiness of the substrate relative to itself. After application the substrate is permitted to fully polymerize and thus cure and harden to form a cast material.

Another form of the method calls for providing a curable resin coated sheet wherein the sheet provides laminable adjacent layers after immersion in a bath. Gloves are donned which gloves are provided with a substantially dry coating which when wetted in said bath is lubricous. The resin is activated by immersion in said bath and the thus activated substrate and resin is wrapped about the patient's limb using the gloves. The resin is then permitted to cure to laminate at least two adjacent layers of the sheet.

BRIEF DESCRIPTION OF THE DRAWING

The invention will now be described with reference to the accompanying drawings wherein.

DETAILED DESCRIPTION OF THE INVENTION

Figure 1:
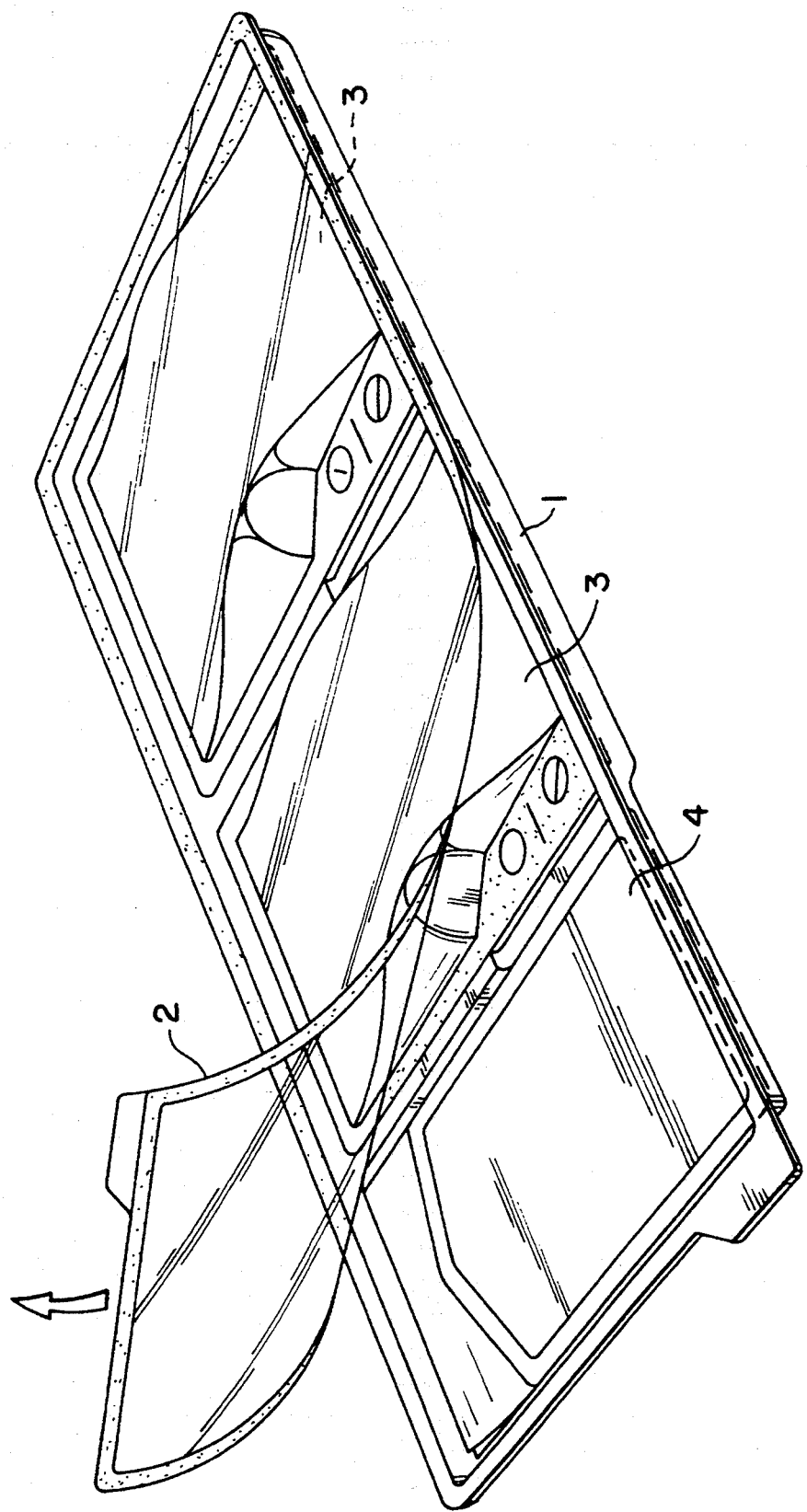
FIG. 1 is a perspective view of a package containing the materials for use in the present method.
Figure 2:
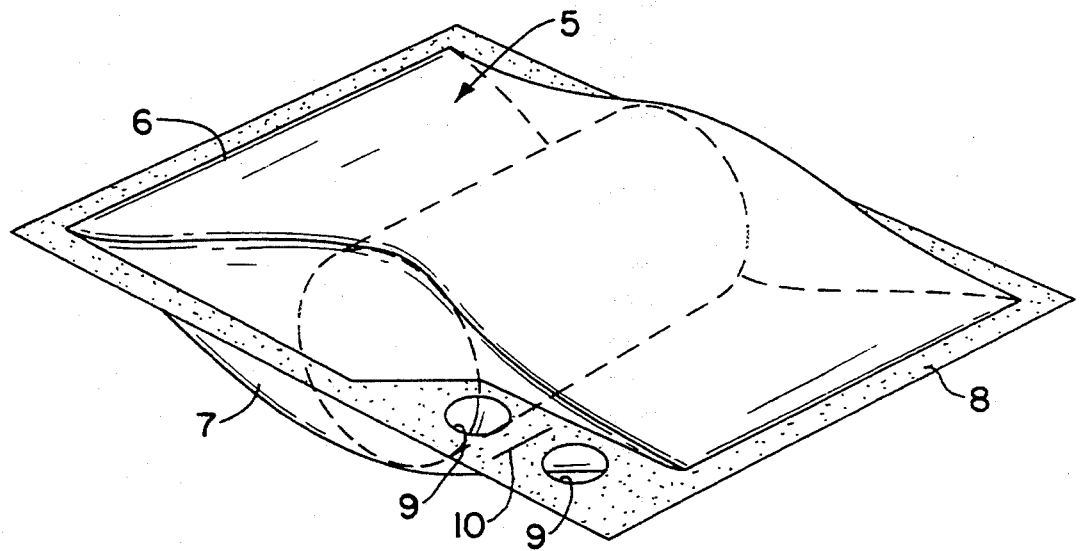
FIG. 2 shows a package containing a resin coated substrate for use as an orthopaedic bandage.

FIG. 1 depicts a kit-like structure in which the supplies for the method of the present invention are supplied. In particular a shell (1) having a peelable layer (2) defining a sealed inner volume is provided. The shell may be formed so as to provide as many compartments as necessary for providing the kit. In particular as shown in FIG. 1 compartments (3) are provided for containing orthopaedic bandage material and compartment (4) is provided in order to supply at least one pair of coated gloves.

In use the package is opened by peeling peelable layer (2) away from shell (1) exposing the packages of orthopaedic bandage and gloves. The package (5) is removed and contains a roll of predetermined length of orthopaedic bandage material having uncured prepolymer resin deposited thereon. The bandage may be, for example, a knitted fiberglass substrate having a polyurethane prepolymer thereon such as the bandage sold by Johnson & Johnson Orthopaedics under the trade name Delta-Lite ® fiberglass casting tape. The package (5) is formed of a top sheet (6) and bottom sheet (7) which are sealed about their periphery by, for example, heat sealing to form a unitary package. Sealed portion (8) widens at one corner to provide space to define openings (9) which are positioned on opposite sides of slit (10).

Figure 3:
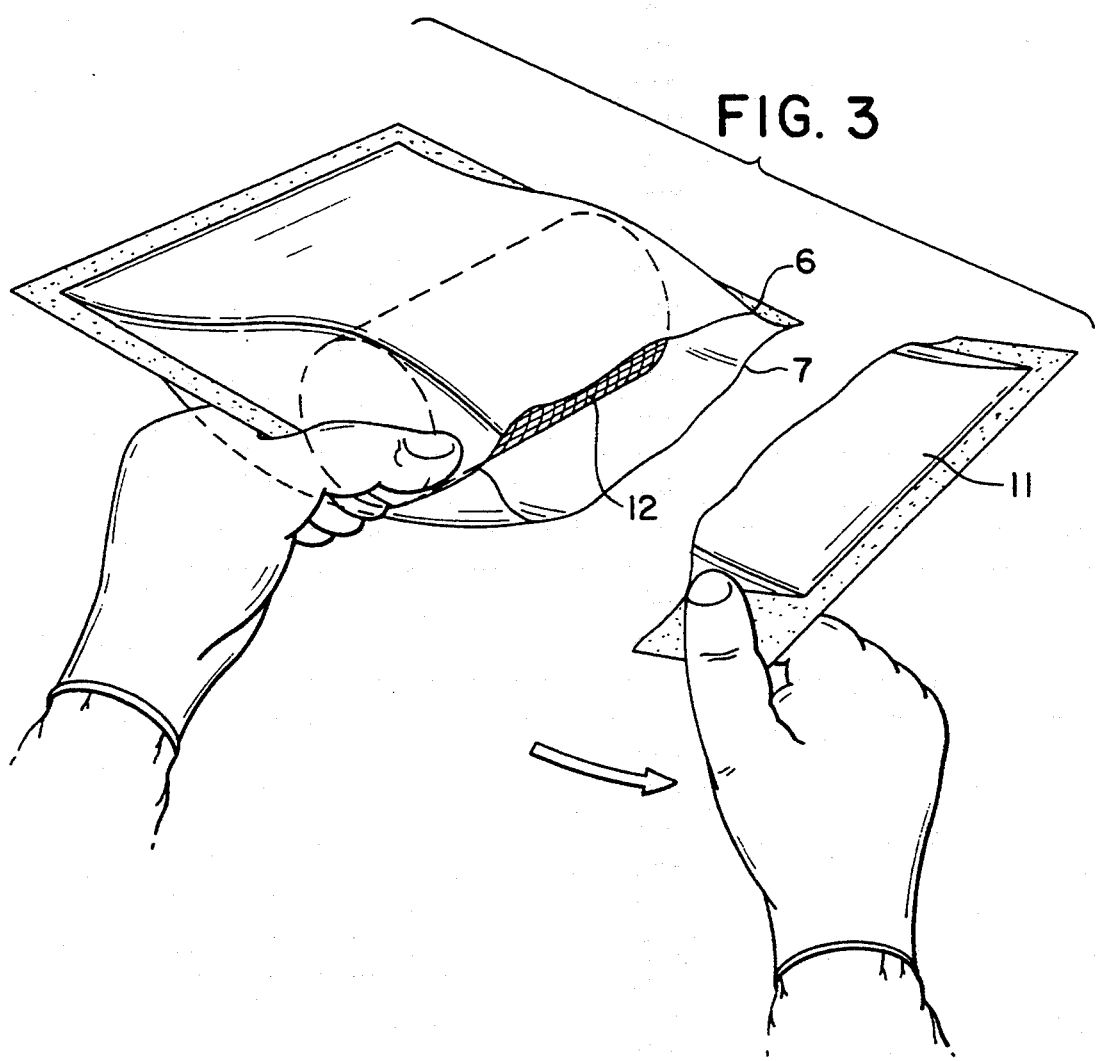
FIG. 3 shows the package of FIG. 2 being opened.
Figure 4:
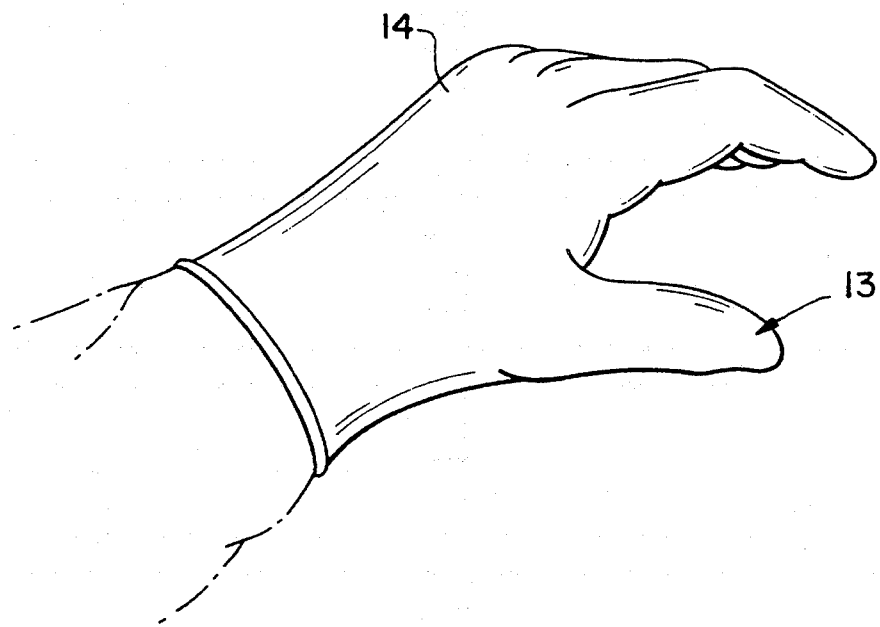
FIG. 4 depicts the glove of the present invention used in the method of the present application.
Figure 5:
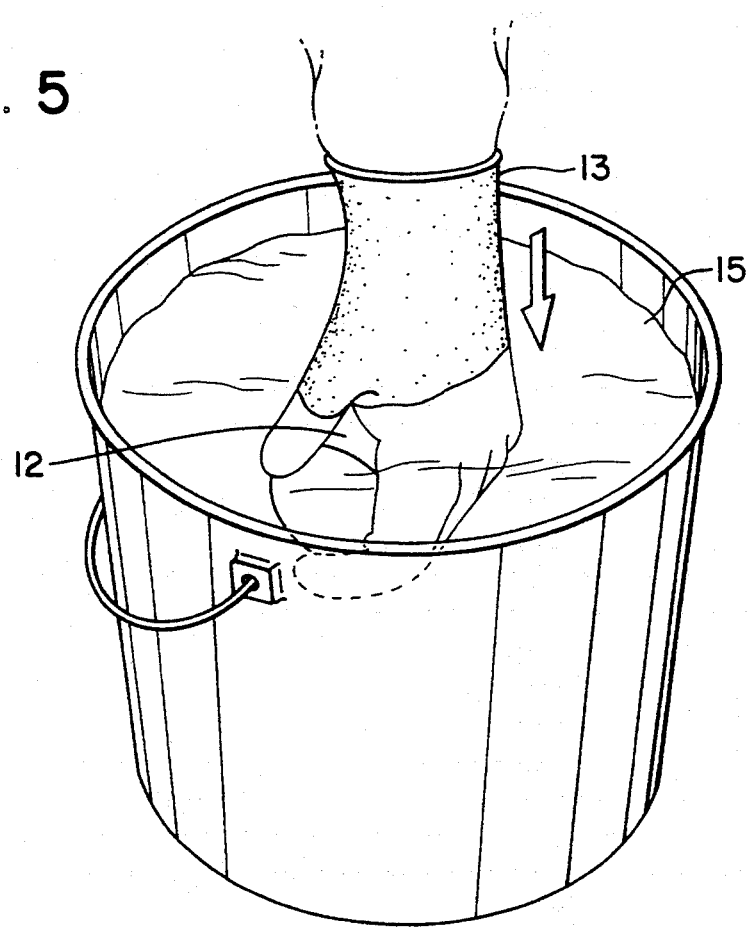
FIG. 5 shows the immersion of the orthopaedic material by the glove covered hand in a bath to activate the material.
Figure 6:
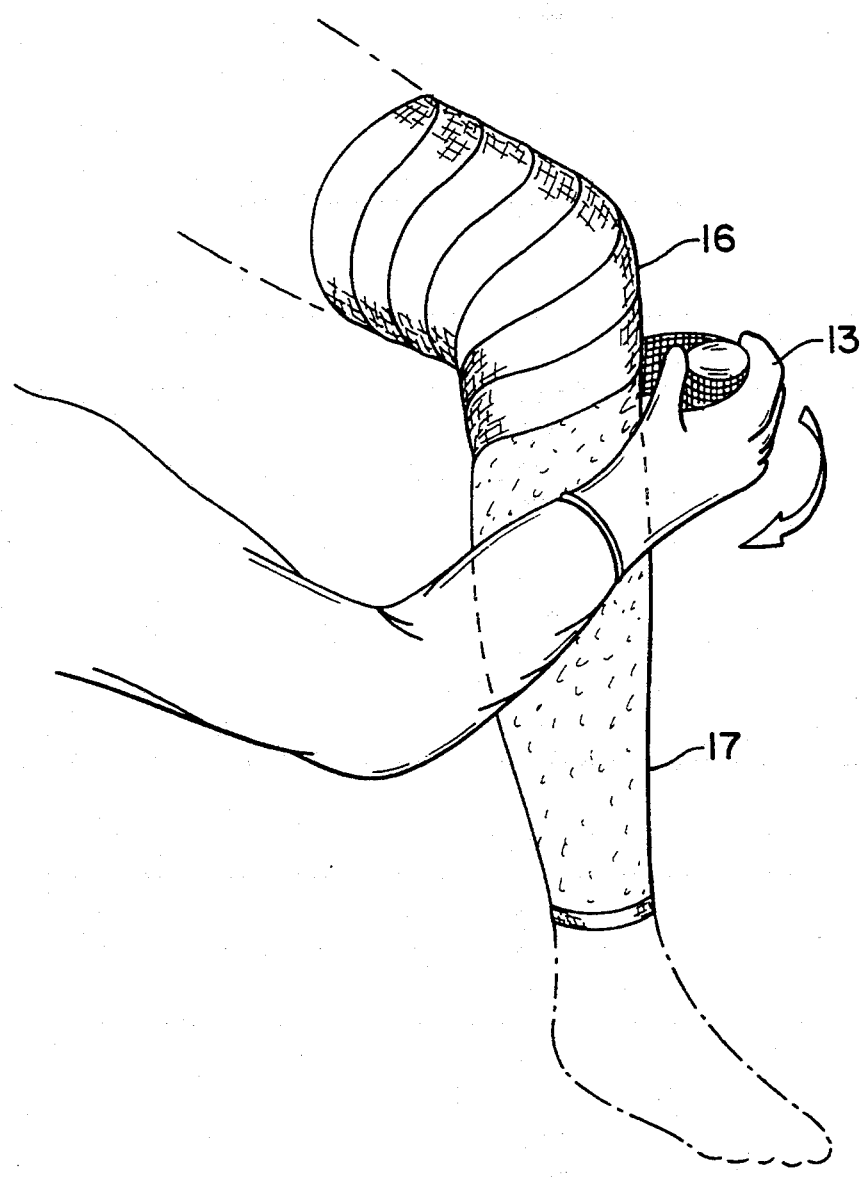
FIG. 6 shows wrapping of the material about the limb of a patient in order to apply the material thereto.

In use the package may be opened during the application of the orthopaedic bandage to the limb of the patient. In such a situation the applier would already be wearing the gloves of the invention, which will be described below, in order to provide a lubricous contact between the hands of the applier and the orthopaedic bandage material. In order to facilitate the opening of the package, openings (9) permit points at which the applier may grasp the package either by insertion of a finger or by contact of the fingers in a gripping fashion through the opening so that the hands are not slipping on the outer surface of the package. Slit (10) provides a start for the opening tear of the package as well as a stress point to facilitate opening of the package. A portion of the package is torn away as shown in FIG. 3 and waste section (11) is discarded.

Thus opened the applier is provided access to a roll (12) of orthopaedic bandage material having thereon a prepolymer coating.

Glove (13) has an outer surface (14) having thereon a substantially dry coating which forms a lubricous surface when wetted during the application of the bandage as is described below. This glove may be formed of any suitable substance such as for example butyl rubber, latex, polyvinyl chloride polyvinyl alcohol, neoprene or other natural or synthetic polymeric materials.

The coating is applied to the glove substantially as described in U.S. Pat. No. 4,100,309. The coating may be, for example, polyvinyl pyrollidone which is applied in a non-water based solvent carrier as follows. Preformed latex rubber gloves are mounted in multiple clamping devices on a rack where the gloves are pressurized with air in order to partially inflate them and fully expose the gloves' outside surfaces. The rack is lowered into position so that the inflated gloves dip into a container of the solvent carrier solution for a period of time sufficient to completely wet the outside surfaces of the gloves. The rack, with attached gloves, is removed from its position above the dip bath and placed in an oven where solvent is allowed to evaporate and the resultant coating on the gloves is heated to facilitate curing.

The coating may also be provided in a water based fashion as follows. A machine for the continuous manufacture of latex rubber gloves is equipped with an additional dip tank positioned at the end of the line so that the latex gloves, prior to final drying, are subjected to an overdip of an aqueous based formulation in order to provide the coating to the glove, described above.

The coating applied to the gloves as an overdip at the end of the latex glove manufacturing line is applied from an aqueous bath whose solids (non-aqueous) components make up 14% of the total bath. These components are:

| Component | % of Total |
| --- | --- |
| 2-Pyrol (GAF) | 78.5 |
| Desmodur XP7005 (Mobay) | 1.8 |
| Glycerine (Dial) | 2.3 |
| Igepal CO-630 (Rhone Polenc) | 3.6 |
| Polyvinyl Pyffollidone K-90 (GAF) | 11.5 |
| Kelco K7C233 (Kelco) | 1.4 |
| Impranil DLN (Mobay) | 0.4 |
| Neorez R-962 (ICI) | 0.5 |
| | 100.0 |

If a distinctively colored glove is desired, a pigment may be added to the above overdip bath or to the bath preceding the overdip bath on the production line. For example, if a light blue colored glove is desired one can add 0.02% Stan-Tone ® 40WD01 Blue (Harwick Chemical Corp) to the latex substrate. This results in a finished glove with an attractive blue color, after the overdip coating has been accomplished.

Over Dip Coating Composition of Solids in Aqueous Systems 1. 2-Pyrol (GAF)—2-pyrrolidone 2. Desmodur XP7005 (Mobay)—Blocked Aromatic Isocyanate Prepolymer
3. Glycerine (Dial Corp)—Glycerine
4. Igepal CO-630 (Rhone Polenc)—Surfactant Nonylphenyxy poly(ethyleneoxy)ethanol
5. PVP/K-90 (GAF)—Polyvinylpyrollidone
6. Kelco K7C233 CKelco)—Sodium alginate (Hydrophilic colloid)
7. Impranil DLN (Mobay)—Artionic aqueous dispersion of an aliphatic polyester polyurethane
8. Neorez R-962 (ICI)—Aqueous dispersion of an aliphatic polyurethane Upon donning glove (13) and opening the package as described above, access is gained to the orthopaedic bandage material. The orthopaedic bandage material is immersed in a bath (15) which may conveniently be water if a prepolymer is used which is activatable by immersing in water. The coating on the surface (14) of glove (13) is also in a manner activated by the water of the bath. The surface is such that when wetted by the bath it becomes significantly more lubricous than it was prior to being wetted. This lubricousness relative to the resin impregnated orthopaedic bandage permits the application of the bandage (16) over a stockinette (17) in a known manner. The bandage (16) adheres to itself in order to maintain its laminable position while at the same time being handled by a glove (13) having a lubricous surface which permits an easily slidable handling of the orthopaedic material by the glove covered hand.

What is claimed is:

1. A method of immobilizing a patient's limb comprising;
   a) immersing a substrate having a water activatable setting and adhering substance impregnated thereon in a bath of water;
   b) applying said substrate to said limb using gloves having a coating thereon which becomes lubricous when wetted with water which coating does not substantially effect the activatable and adhering substance; and
   c) permitting the setting and adhering substance to cure.

2. The method according to claim 1 wherein
   a) the substrate is an open weave fibrous structure; and
   b) the setting and adhering substance is a polyurethane prepolymer.

3. The method according to claim 1 further comprising;
   a) donning said gloves prior to removing said substrate from said bath; and
   b) immersing said gloves in the bath to wet said coating.

4. The method according to claim 3 further comprising:
   a) opening at least one package containing said substrate after wetting of said coating.

5. The method of claim 1 further comprising:
   a) donning said gloves prior to immersing said substrate; and
   b) holding said substrate at least part of the time it is immersed by said gloves to activate said setting and adhering substance simultaneously with wetting said coating.

6. A method of applying an orthopaedic bandage material comprising:
   a) providing an activatable substrate impregnated with a polymerizable material which impregnated substrate is self adhering;
   b) activating said polymerizable material by emersion in a bath;
   c) donning gloves having an outer coating which is activated by said bath to provide a lubricous surface to said gloves;
   d) wrapping the activated substrate about a patient's limb using said gloves to assist in the application while reducing the tackiness of the substrate relative the gloves without reducing significantly the tackiness of the substrate relative itself; and
   e) permitting the polymerizable material to cure.

7. A method of applying an orthopaedic bandage material comprising:
   a) providing a curable resin coated sheet wherein said sheet provides laminable adjacent layers after immersion in a bath to activate curing of the resin;
   b) donning gloves which are provided with a substantially dry coating which is lubricous when wetted by said bath;
   c) activating said resin by immersion in said bath;
   d) wrapping the activated substrate about a patient using said gloves; and
   e) permitting said resin to cure to laminate at least two adjacent layers of said sheet.

8. The method according to claim 7 further comprising:
   a) immersing said resin coated sheet in said bath by use of said gloves; and
   b) said coating on said gloves is hydrophilic.

9. The method according to claim 8 wherein
   a) said coating on said gloves is polyvinylpyrrolidone.

10. The method according to claim 9 further comprising
    a) applying said substrate to a patient's limb.

* * * * *